United States Patent [19]

Mussinan et al.

[11] 4,275,080

[45] Jun. 23, 1981

[54] FLAVORING WITH 8-P-CYMENYL-ETHYL ETHER

[75] Inventors: Cynthia J. Mussinan, Bricktown; Braja D. Mookherjee, Holmdel; Manfred H. Vock, Locust; Frederick L. Schmitt, Holmdel, all of N.J.; Edward J. Shuster, Brooklyn, N.Y.; James M. Sanders, Eatontown, N.J.; Bette M. Light, Highlands, N.J.; Edward J. Granda, Englishtown, N.J.

[73] Assignee: International Flavors & Fragrances Inc., New York, N.Y.

[21] Appl. No.: 88,571

[22] Filed: Oct. 26, 1979

Related U.S. Application Data

[62] Division of Ser. No. 12,798, Feb. 16, 1979, which is a division of Ser. No. 939,897, Sep. 5, 1978, Pat. No. 4,163,068, which is a division of Ser. No. 872,937, Jan. 27, 1978, Pat. No. 4,131,687.

[51] Int. Cl.$^3$ .............................................. A23L 1/226
[52] U.S. Cl. ......................................... 426/3; 426/538
[58] Field of Search ..................... 426/3, 538; 568/579

[56] References Cited

U.S. PATENT DOCUMENTS

| 3,993,604 | 11/1976 | Thomas ........................... 568/579 X |
| 4,131,687 | 12/1978 | Mussinan et al. ................ 426/538 X |
| 4,163,068 | 7/1979 | Mussinan et al. .................... 426/538 |

OTHER PUBLICATIONS

Arctander, Perfume and Flavor Chemicals, vols. I-II, 1969, Published by the Author: Montclair, N.J., Items No. 573-577, 752-757, 819, 2446, 2732-2734, 2738-2739, 2741, 2944-2948.
C.A., vol. 83, 1975, 25073c.

*Primary Examiner*—Joseph M. Golian
*Attorney, Agent, or Firm*—Arthur L. Liberman

[57] ABSTRACT

Described are processes for flavoring foodstuffs, chewing gums, medicinal products and toothpastes using as the essential ingredient 8-p-cymenyl ethyl ether which is synthetically produced and substantially pure.

1 Claim, 12 Drawing Figures

GLC PROFILE A FOR EXAMPLE I

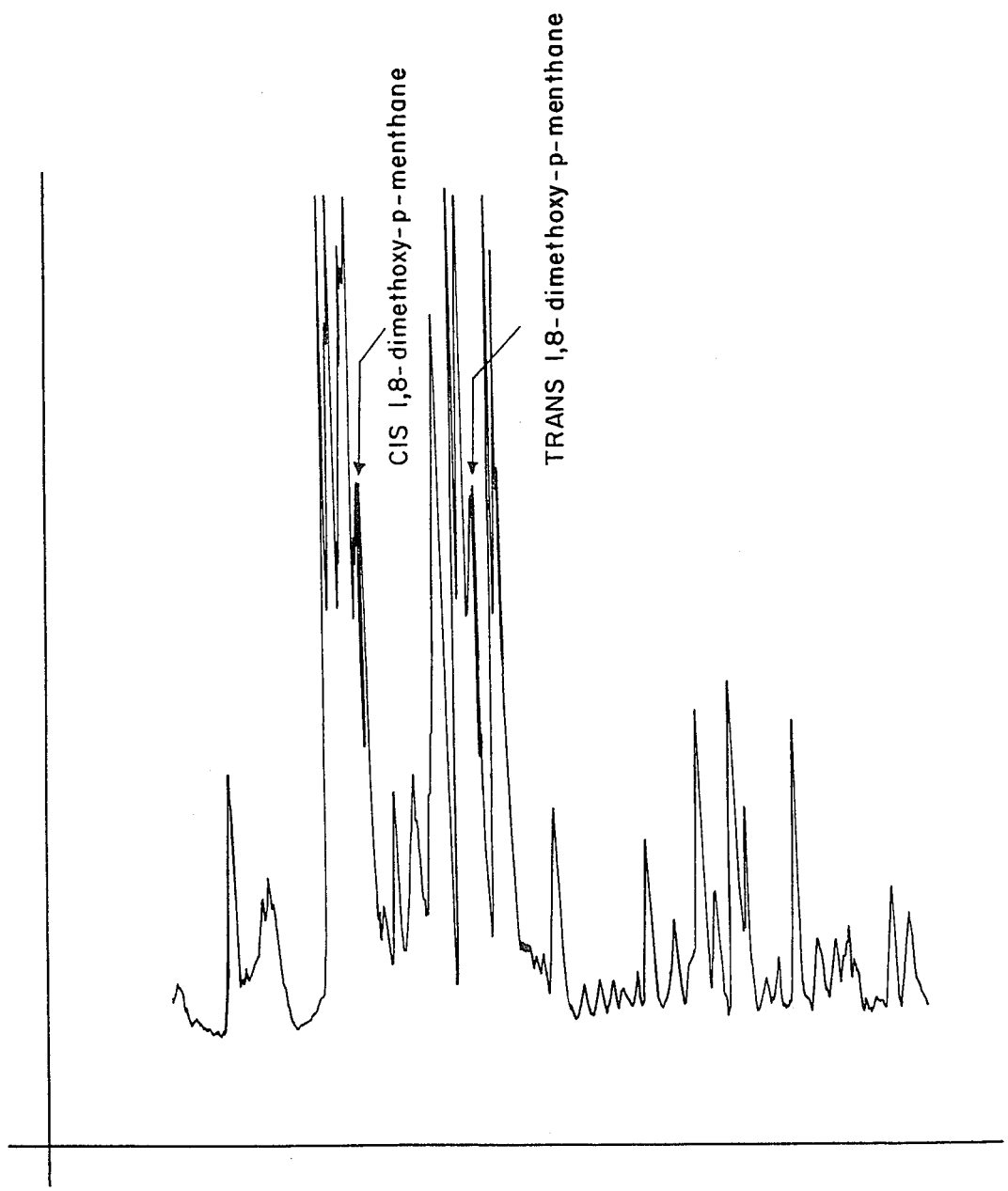
FIG.IA
GLC PROFILE FOR EXAMPLE I

MASS SPECTRUM FOR CARVYL ETHYL ETHER
EXAMPLE I & EXAMPLE II

MASS SPECTRUM FOR 8-P-CYMENYL ETHYL ETHER
EXAMPLE I & EXAMPLE II

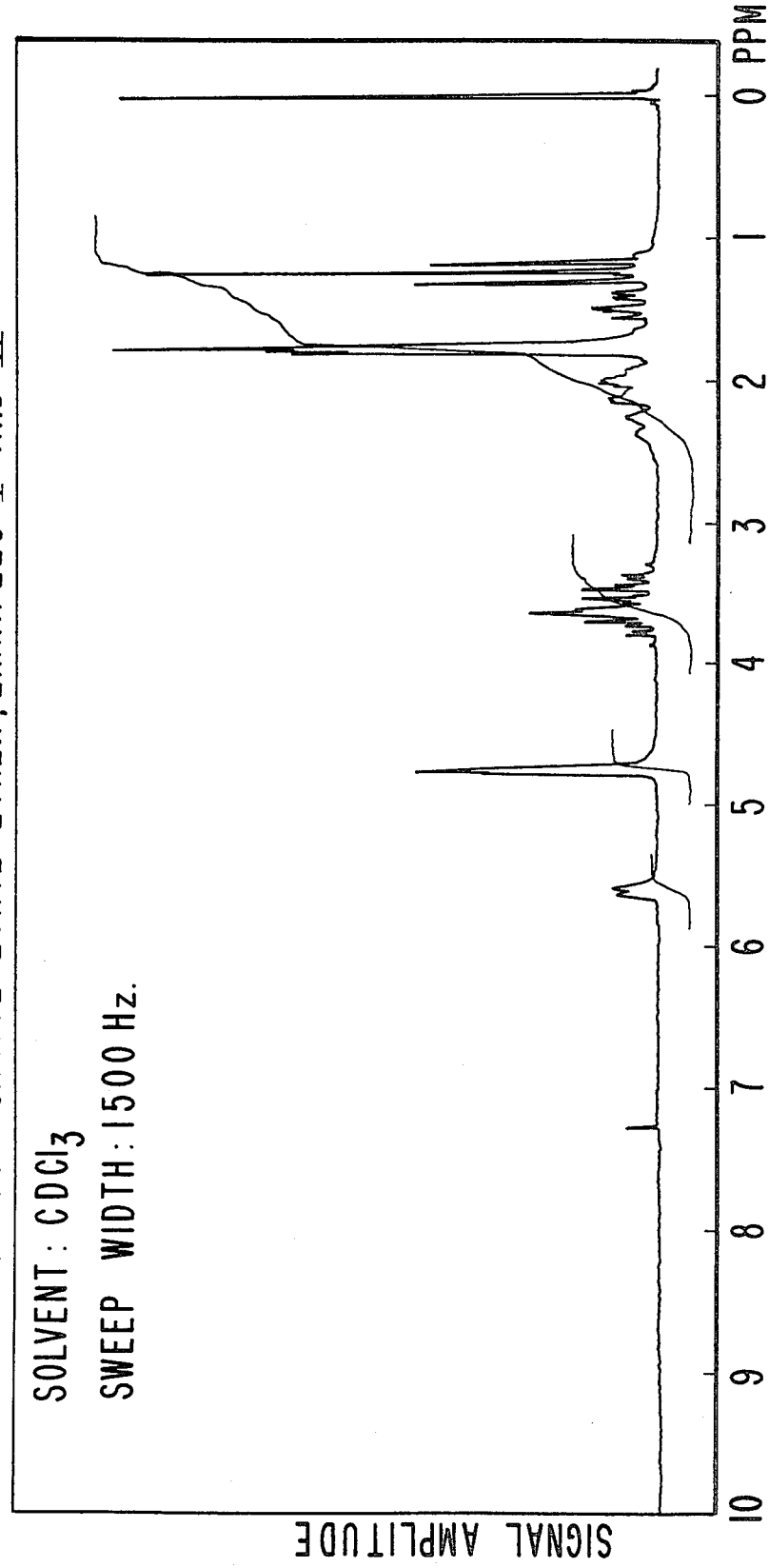

IR SPECTRUM FOR CARVYL ETHYL ETHEL, EXAMPLES I AND II

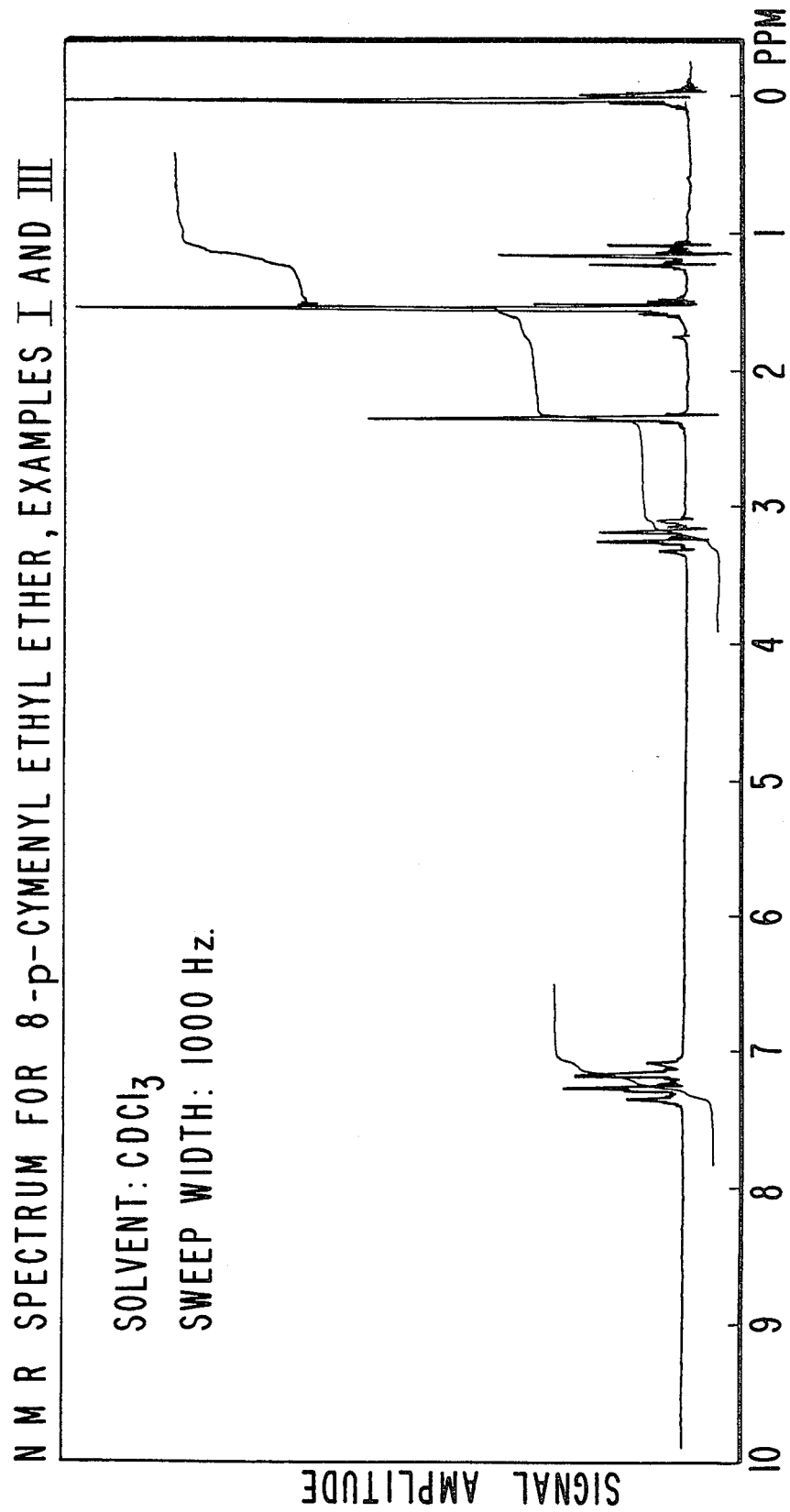

IR SPECTRUM FOR 8-p-CYMENYL ETHYL ETHER, EXAMPLES I AND III

GLC PROFILE B EXAMPLE I

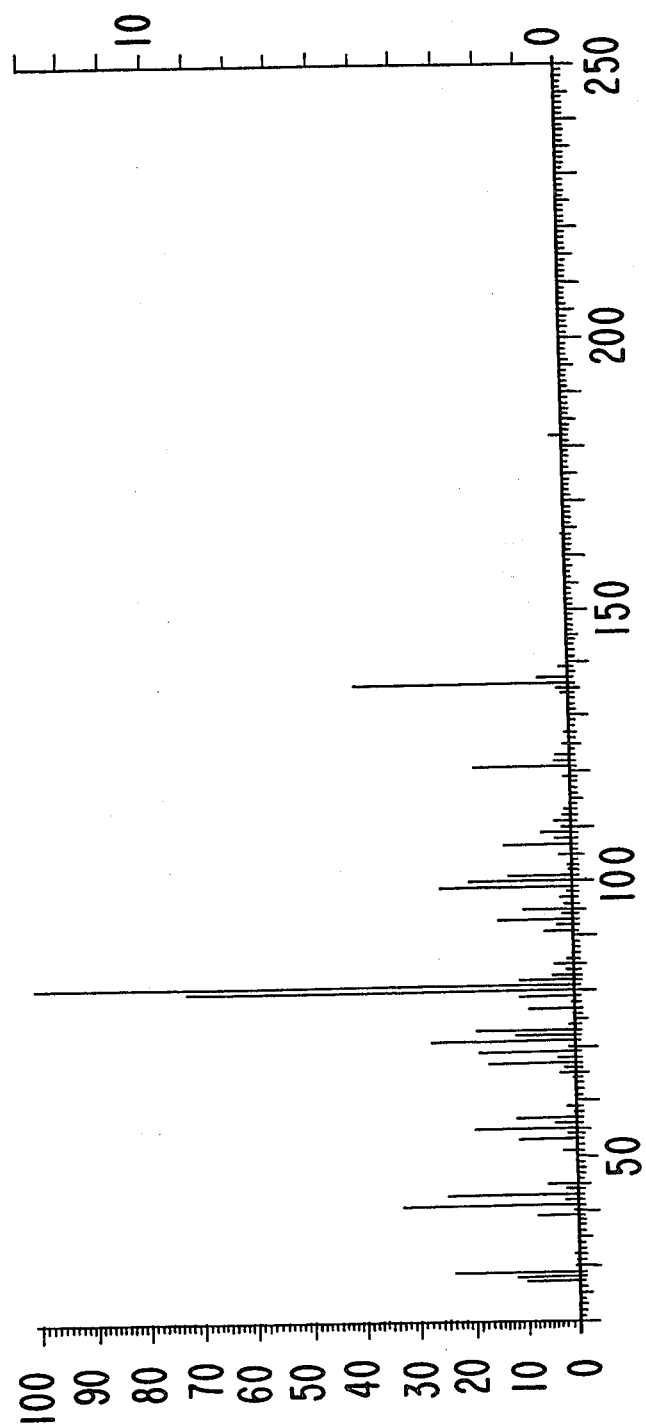

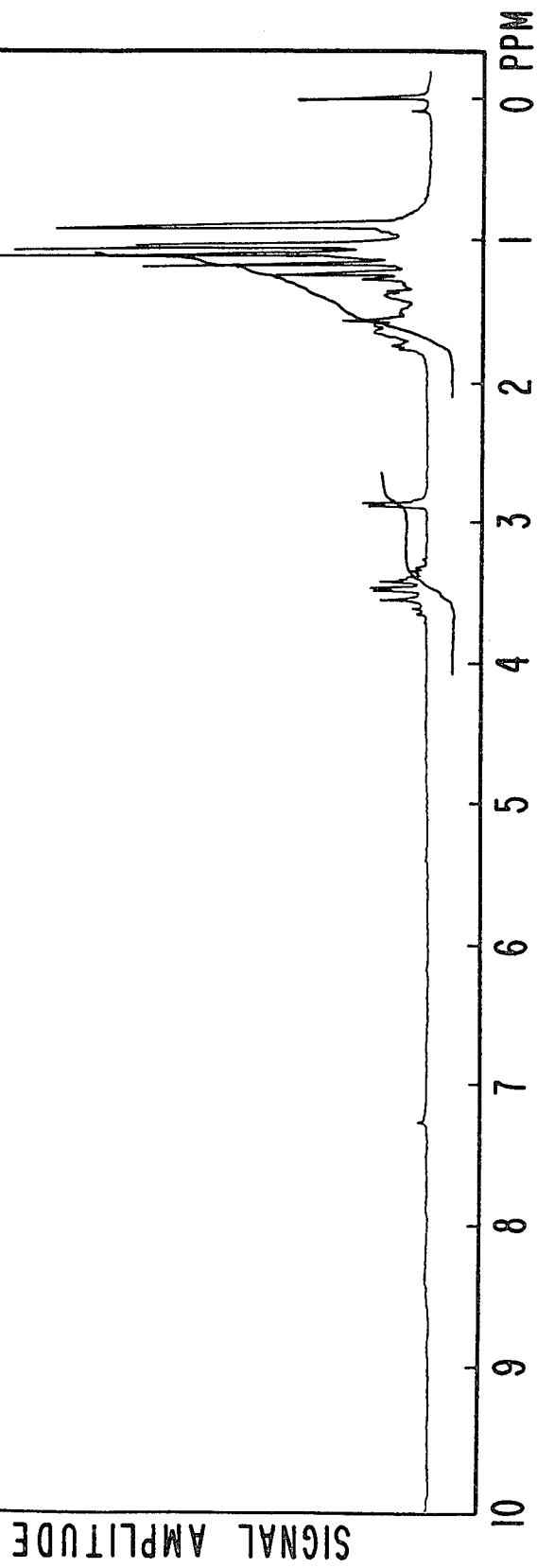

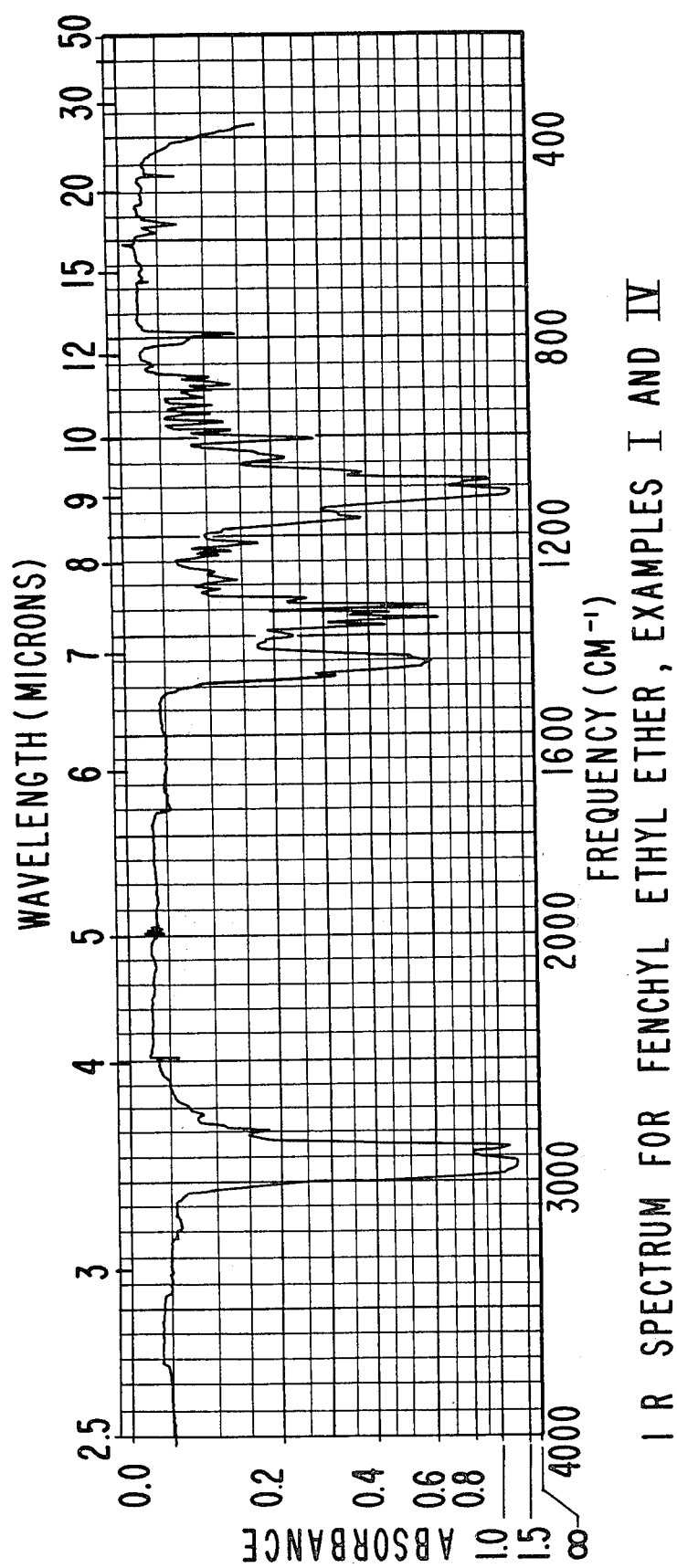

FLAVORING WITH 8-P-CYMENYL-ETHYL ETHER

This application is a divisional of application for United States Letters Patent Ser. No. 012,798 filed on Feb. 16, 1979, which in turn, is a divisional of application for United States Letters Patent Ser. No. 939,897, filed on Sept. 5, 1978, now U.S. Pat. No. 4,163,068, issued on July 31, 1979, which, in turn, is a divisional of application for United States Letters Patent Ser. No. 872,937, filed on Jan. 27, 1978, now U.S. Pat. No. 4,131,687, issued on Dec. 26, 1978.

BACKGROUND OF THE INVENTION

The instant invention provides novel $C_{10}$-terpenyl ethers having the structure:

wherein the terpene moiety has one of the structures:

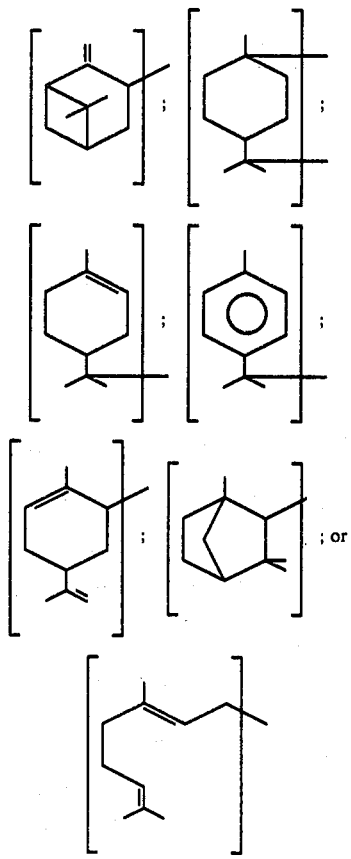

and the moiety $R_1$ is $C_1$–$C_4$ alkyl, $C_3$ or $C_4$ alkenyl, $C_3$ haloalkenyl or $C_3$ alkynyl, and uses thereof for their organoleptic properties in consumable materials.

Materials which can provide green citrus, limey, lemony, piney, tart, herbaceous, floral, sweet anise, borneol-like, earthy carrot, petitgrain-like, grapefruit, deep woody, animal, sandal-like woody, fruity, floral, camphoraceous, and rosemary-like notes with basil-like, carvone-like, chamomile-like, and vanillin-like nuances and sweaty undertones are known in the art of perfumery. Many of the natural materials which provide such fragrances and contribute desired nuances to perfumery compositions are high in cost, vary in quality from one batch to another and/or are generally subject to the usual variations of natural products. By the same token materials which can provide sweet, fruity, berry-like, minty, green, herbal, musty, vegetable (especially celery), spicey, earthy, anise-like, aniseed, fresh fennel, strawberry-like, citrus peel-like (especially orange peel), citrus, coriander-like, licorice, floral, rosey, woody, parsely, grapefruit-like, cumin-like, eucalyptol-like, cedarwood-like, oakwood-like, lemon juice-like, camphoraceous, blueberry, sassafrass, and rooty aroma notes with nutty, fruity, berry-like, minty, bitter, musty, waxy, green, herbal, woody, vegetable (especially celery-like), earthy, sweet, spicey, anise-like, aniseed, fresh fennel, strawberry, citrus peel (especially orange peel), citrus-like, floral, rosey, woody, parsley grapefruit-like, cumin-like, coriander-like, eucalyptol-like, green pea, lemon juice-like, cedarwood like and steamed oak flavor notes having sour effects, astringent effects, mouthfeel effects and biting effects are well known in the art of flavoring for foodstuffs, toothpastes, chewing gums and medicinal products. Many of the natural materials which provide such flavor notes and contribute desired nuances to flavorant compositions are high in cost, vary in quality from one batch to another and/or are generally subject to the usual variations of natural products.

There is, accordingly, a continuing effort to find synthetic materials which will replace enhance or augment the essential flavor and fragrance notes provided by natural essential oils or compositions thereof. Unfortunately many of these synthetic materials either have the desired nuances only to a relatively small degree or else contribute undesirable or unwanted odor to the compositions. The search for materials which can provide a more refined licorice-like flavor, for example, has been difficult and relatively costly in the areas of both natural products and synthetic products.

Artificial flavoring agents for foodstuffs have received increasing attention in recent years. For many years such food flavoring agents have been preferred over natural flavoring agents at least in part due to their diminished cost and their reproducible flavor qualities. For example, natural food flavoring agents such as extracts, concentrates and the like are often subject to wide variations due to changes in quality, type and treatment of the raw materials. Such variations can be reflected in the end products and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums and toothpastes is not completely known. This is noticable in products having licorice, citrusy and vegetable flavor characteristics particularly.

Even more desirable are products that can serve to substitute for difficult-to-obtain natural perfumery oils and at the same time substitute for natural flavoring ingredients in foodstuffs, chewing gums, medicinal products and toothpastes.

In U.S. Pat. No. 3,993,604 issued on Nov. 23, 1976, Thomas and Ohloff disclose a process for improving, enhancing, or modifying the organoleptic properties of perfumes, perfumed products, natural or artificial essential oils which comprises adding thereto a small but effective amount of at least one compound of the formula:

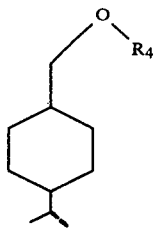

wherein $R_4$ is hydrogen, alkyl or acyl containing from one up to six carbon atoms and the dashed line represents a carbon-carbon single bond or a carbon-carbon double bond. The compounds of U.S. Pat. No. 3,993,604 are, however, different in kind insofar as their organoleptic qualities and aroma and flavor intensities are concerned from the $C_{10}$-terpenyl ethers of the instant case.

A number of the methyl ethers of $C_{10}$-terpenes are known, for example, the methyl ether of Carveol (Beilstein, Vol. VI, syst. No. 510) and 1,8-dimethoxy-p-menthane (Royals, J. Am. Chem. Soc., 71, 2563-71 (1949)). In addition, the methyl ether of p-cymen-8-ol is known as an oxygenated constituent of the essential oil of black pepper as disclosed in Bull. Soc. Chim. Belg. 1975, 84(3), 167-77 (abstracted in Chem Abstracts 83:25073c). The ethyl ether of p,α-dimethylphenethyl alcohol is disclosed at Chem Abstracts 70:57320d.

Burczyk at Chem Abstracts 74:13285z discloses a number of methyl ethers of $C_{10}$-terpenes having the following structures:

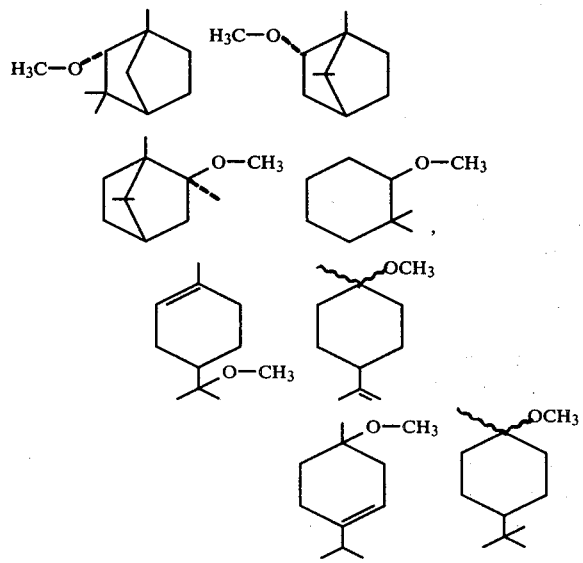

However, the usefulness for augmenting or enhancing the organoleptic properties of perfumes, perfumed articles, colognes, foodstuffs, chewing gums, toothpastes or medicinal products of the terpene ethers as disclosed herein is neither expressly nor implicitly set forth in any of the references set forth above.

Arctander, "Perfume and Flavor Chemicals (Aroma Chemicals)" 1969, discloses at No. 696 the organoleptic properties of citronellyl vinyl ether as follows:

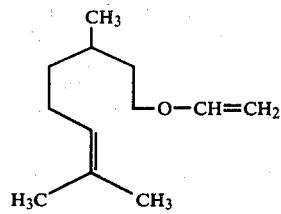

"Colorless liquid. Insoluble in water, soluble in alcohol and oils.

Green-foliage-like, Rose-Geranium type, fresh and rather powerful odor of modest tenacity.

Useful in Citrus cologne types, soap perfumes (as a diffusive and refreshing topnote ingredient), as a supporting item for Geranium notes, etc."

At No. 1961 (Vol. II) of Arctander, methyl citronellyl ether is disclosed for its organoleptic properties as follows:

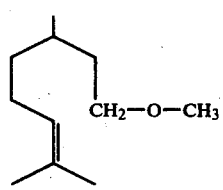

"Colorless liquid.

Insoluble in water, soluble in alcohol and oils.

Fresh-rosy, green-leafy type of odor with a "wet vegetable" note of attractive naturalness. Moderate to poor tenacity.

This ether has been suggested for use in perfume compositions, but it is rarely offered commercially, although many ethers of Citronellol, Geraniol, Linalool and related alcohols have been prepared in search of new floral-green materials. Quite a large number of these ethers have very interesting and attractive odors, and it is rather surprising that very few are offered commercially.

The title ether could find use in modern fragrances, particularly as part of novel topnote complexes with Citrus, Galbanum or fresh-herbaceous materials, fruity notes, etc.

It blends very well with Bergamot, Estragon, Basil, Verbena and other distinguished topnote materials, and it is tolerated in the perfume composition at quite surprising concentrations. In other words, its pleasant level of application has a very considerable "range" from less than one percent up to 10 or 15%, in exceptional cases even higher than that."

However, nothing in the Arctander references discloses the unexpected, unobvious and advantageous organoleptic properties of the $C_{10}$-terpenyl ethers of the instant invention.

BRIEF DESCRIPTION OF THE DRAWINGS

FIG. 1A is a section of the GLC profile showing the presence of cis- and trans-1,8-dimethoxy-p-methane in lemon juice and described in Example I.

FIG. 3 represents the NMR (nuclear magnetic resonance) spectrum for carvyl ethyl ether produced according to Examples I and II.

FIG. 6 represents the NMR spectrum for 8-p-cymenyl ethyl ether produced according to Examples I and III.

FIG. 9 represents the mass spectrum for fenchyl ethyl ether produced according to Examples I and IV(B).

FIG. 10 represents the NMR spectrum for fenchyl ethyl ether produced according to Examples I and IV(B).

FIG. 11 represents the infrared spectrum for fenchyl ethyl ether produced according to Examples I and IV(B).

THE INVENTION

Figure 1:
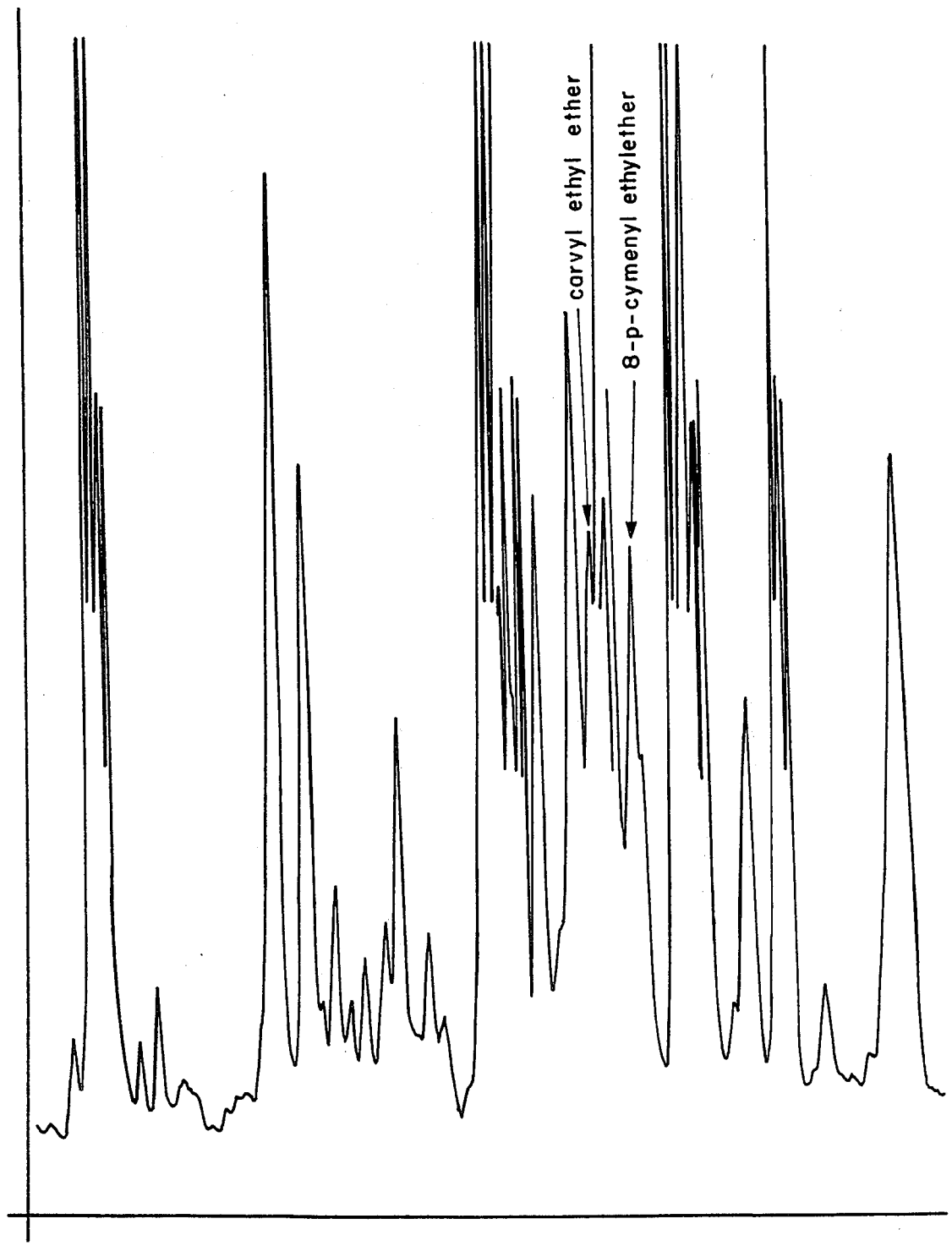
FIG. 1 is a section of the GLC profile showing the presence of carvyl ethyl ether and 8-p-cymenyl ethyl ether in lemon juice as described in Example I.

It has now been determined that certain $C_{10}$-terpenyl ethers are capable of imparting a variety of flavors and fragrances to various consumable materials and are also capable of augmenting or enhancing a variety of flavors and fragrances of various consumable materials. Briefly our invention contemplates augmenting or enhancing the flavors and/or fragrances of such consumable materials as perfumes, perfumed articles, colognes, foodstuffs, chewing gums, toothpastes and medicinal products by adding thereto a small but effective amount of at least one $C_{10}$-terpenyl ether having the structure:

$$(C_{10}\text{-TERPENYL-O-R}_1)_n$$

wherein n is 1 or 2 and wherein the terpene moiety has one of the structures:

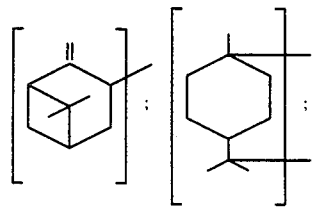

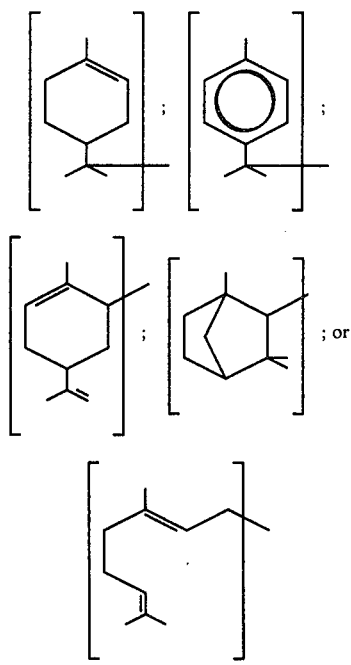

wherein $R_1$ is $C_1$–$C_4$ alkyl, $C_3$ or $C_4$ alkenyl, $C_3$ haloalkenyl, or $C_3$ alkynyl.

The $C_{10}$-terpenyl ethers of our invention augment or enhance sweet, fruity, berry-like, minty, green, herbal, musty, vegetable (especially celery), spicey, earthy, anise-like, aniseed, fresh fennel, strawberry-like, citrus peel-like (especially orange peel), citrus, coriander-like, licorice, floral, rosey, woody, parsely, grapefruit-like, cumin-like, eucalyptol-like, cedarwood-like, oakwood-like, lemon juice-like, camphoraceous, blueberry, sassafrass, and rooty aroma characteristics and nutty, fruity, berry-like, minty, bitter, musty, waxy, green, herbal, woody, vegetable (especially celery-like), earthy, sweet, spicey, anise-like, aniseed, fresh fennel, strawberry, citrus peel (especially orange peel), citrus-like, floral, rosey, woody, parsley, grapefruit-like, cumin-like, coriander-like, eucalyptol-like, green pea-like, lemon juice-like with sour and astringent mouthfeel and biting effects insofar as augmenting or enhancing the aroma or taste of foodstuffs, toothpastes, medicinal products and chewing gums. The $C_{10}$-terpinyl ethers of our invention also augment or enhance the green citrus, limey, lemony, piney, tart, herbaceous, floral, sweet anise, borneol-like, earthy carrot, petitgrain-like, grapefruit, deep woody animal, sandal-like woody, fruity, floral, camphoraceous, and rosemary/lavander-like notes of perfumes, perfumed articles and colognes and augment, enhance or impart basil-like, carvone-like, chamomile-like, and/or vanillin-like nuances with sweaty undertones.

Examples of the $C_{10}$-terpenyl ethers of our invention and their organoleptic characteristics are as follows:

TABLE I

| STRUCTURE OF COMPOUND | NAME OF COMPOUND | FLAVOR CHARACTERISTICS | FRAGRANCE CHARACTERISTICS |
|---|---|---|---|
| | Geranyl butyl ether | Citrus, floral, rosey aroma characteristics with citrus, nutty, floral, rosey and bitter flavor characteristics | A green citrus, lemony, floral aroma |
| | Carvyl ethyl ether | A woody, green, parsley-like, celery-like and grapefruit-like aroma characteristic with woody, green, green pea-like, celery-like, citrus flavor characteristics and a sour and astringent effect | An earthy, carrot topnote giving way to a petitgrain character with basil/carvone nuances |
| | 8-p-cymenyl-ethyl ether | An herbal, coumarin-like and green aroma characteristic with herbal, cumin-like, lemon juice-like, green, and oily flavor characteristics | A sweet, phenolic, cymene-like, acetophenone-like aroma with a musty, vanilla, anthranilate note |
| | fenchyl ethyl ether | A woody, cedarwood-like, oakwood-like, lemon juice-like, camphoraceous, herbaceous, citrus-like, blueberry-like, sassafrass and rooty aroma characteristic with woody, cedarwood-like, steamed oak, camphoraceous, herbaceous, citrusy, woody, blueberry, sassafrass-like and rooty flavor characteristics and a sour, mouthfeel and astringent effect. | A sweet, camphoraceous, minty, herbaceous, woody, green aroma with a eucalyptus-like undertone. |
| | bornyl methyl ether | | Camphoraceous, herbal, rosemary/lavendar and borneol-like aroma |
| | carvyl methyl ether | A carrot, parsley-like, earthy and herbal aroma characteristic with sweet, carrot-like, earthy, celery-like, herbal, parsley-like flavor characteristics and a biting effect | A fresh, earthy, carrot topnote giving way to a woody, carvone-like caraway, basil note |
| | bornyl ethyl ether | A camphoraceous, woody, cedarwood-like, eucalyptol-like, and blueberry-like aroma characteristic with camphoraceous, woody, eucalyptol-like, blueberry flavor characteristics and an astringent character | A grapefruit topnote which fades quickly to sour and acrid having ultimately a sour, fruity, floral aroma with chamomile nuances. |
| | 3-allyloxy-2(10)-pinene | A sweet, anise-like, green, woody and floral aroma characteristic with an anise, green and woody flavor characteristic | A strong, sweet, anisic, borneol-like note with piney and herbaceous nuances |
| | 2-(2-propynyloxy)-2(10)-pinene | Aniseed, phenyl, coriander, fruity, berry and citrus peel aroma and flavor characteristics | A sweet, floral aroma with a vanillin sweetness and a borneol, sweaty undertone |
| | 3(2-chloroallyloxy)-2(10)-pinene | Sweet, aniseed-like, fresh phenyl, fruity, strawberry, orange peel and citrusy aroma and flavor characteristics | A fatty, creosote-like, citrusy, linalyl acetate-like aroma with musty and phenolic notes |
| | 3-(methallyloxy-2(10)-pinene | A citrus, licorice and spicey aroma characteristic with bitter flavor characteristics | A fruity, anisi lemony aroma with a wood nuance |
| | α-terpinyl methyl ether | A sweet, vegetable celery-like), spicey aroma characteristic with an earthy nuance and a woody, celery-like, earthy flavor characteristic with sweet and spicey nuances | A tart, limey, terpineol-like note |

TABLE I-continued

| STRUCTURE OF COMPOUND | NAME OF COMPOUND | FLAVOR CHARACTERISTICS | FRAGRANCE CHARACTERISTICS |
|---|---|---|---|
| 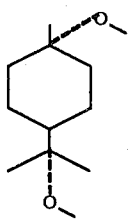 | 1,8-dimethoxy-p-menthane | A sweet, fruity and minty aroma characteristic with green and musty nuances and a nutty, fruity and minty flavor characteristic with bitter, musty, waxy and green nuances | A citrusy note modified by a sweet, sandal-like-woody note |
| 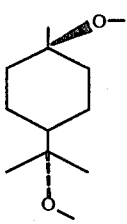 | 1,8-diethoxy-p-menthane | Woody aroma character and woody and bitter flavor characteristics | A green, citrus/lemony, woody aroma |

The 1,8-dimethoxy-p-menthane can exist as a mixture of the cis and trans isomers thereof or can be used as the "cis" isomer having the structure:

or the "trans" isomer having the structure:

The $C_{10}$-terpenyl ethers of our invention can be produced using any one of several known techniques. Thus, the terpenyl alcohol can be reacted with a lower alkanol in the presence of an acid catalyst such as para-toluenesulfonic acid at reflux conditions. As a further example, 8-p-cymenol may be reacted with an excess of ethanol (e.g. from 2 up to 10-fold excess) in the presence of p-toluenesulfonic acid, and the reaction mass may then be refluxed for a period of from 2 up to 10 hours. By the same token carvyl ethyl ether may be produced by reacting ethanol with carveol, the ratio of ethanol:-carveol being about 1 mole ethanol:0.1 moles carveol, and the reaction may take place in the presence of p-toluenesulfonic acid.

The ethers so useful in our invention may also be formed by reacting the corresponding terpenic alcohol with the appropriate sulfate in the presence of sodium hydride in anhydrous media and in the presence of an inert solvent such as dimethyl formamide. Thus, for example, fenchyl alcohol is reacted with diethyl sulfate, the fenchyl alcohol and diethyl sulfate being in a molar proportion of about 1:1 in the presence of sodium hydride and dimethyl formamide.

Compounds having the generic structure:

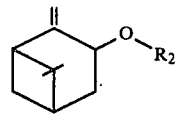

wherein $R_2$ represents $C_3$ or $C_4$ alkenyl, $C_3$ haloalkenyl or $C_3$ alkynyl, may be prepared by reacting pinocarveol with the appropriate organic halide. This reaction is carried out under the influence of a base comprising the step of placing the reactants for the process and the base, respectively, in two immiscible phases; an organic phase and either (i) an aqueous base phase or (ii) a solid base phase with the reactants being located substantially entirely in the first mentioned organic phase and the base being located substantially entirely in the second mentioned phase; and adding to the two phase system a "phase transfer agent" which may be one or more of several organic quaternary ammonium salts.

Specific examples of "phase transfer agents" useful in our invention are as follows:
Tricapryl methyl ammonium chloride;
Cetyl trimethyl ammonium bromide; and
Benzyl trimethyl ammonium hydroxide.

In general, the "phase transfer agents" most preferred have the generic formula:

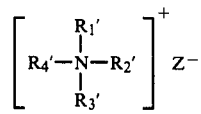

wherein at least one of $R_1'$, $R_2'$, $R_3'$ and $R_4'$ is $C_6$–$C_{14}$ aryl, $C_6$–$C_{10}$ aralkyl, $C_6$–$C_{20}$ alkyl, $C_6$–$C_{14}$ aralkyl and $C_6$–$C_{20}$ alkenyl, and the other of $R_2'$, $R_3'$ and $R_4'$ is alkyl such as methyl, ethyl, n-propyl, i-propyl, 1-butyl, 2-butyl, 1-methyl-2-propyl, 1-pentyl and 1-octyl and Z- is an anion such as chloride, bromide and hydroxide.

This process of our invention is carried out in an inexpensive solvent which is inert to the reaction system, such as toluene, benzene, o-xylene, m-xylene, p-xylene, ethyl benzene, n-hexane, cyclohexane, methylene dichloride and o-dichlorobenzene.

The process of our invention is carried out at a temperature in the range of from about 10° C. up to about 150° C. with a temperature range of 30°-120° C. being preferred. The reaction time is inversely proportional to the reaction temperature, with lower reaction temperature giving rise to greater reaction times; and, accordingly, the reaction time ranges from about 30 minutes up to about 10 hours.

In the reaction of our invention the mole ratio of pinocarveol to organic halide is in the range of from 0.5:1.5 up to about 1.5:0.5 with a preferred ratio of pinocarveol to organic halide being from about 1:1 up to about 1:1.2.

The mole ratio of base to pinocarveol in the reaction mass may be in the range of from about 0.75:1 up to about 1.5:1 with a preferred ratio of base:pinocarveol being from about 1:1 up to about 1.2:1.

The quantity of "phase transfer agent" in the reaction mass based on the amount of pinocarveol in the reaction mass may vary from 0.5 grams per mole of pinocarveol up to 25 grams of "phase transfer agent" per mole of pinocarveol with a preferred concentration of "phase transfer agent" being in the range of from about 2.5 up to about 7.5 grams of "phase transfer agent" per mole of pinocarveol.

This reaction of our invention is preferably carried out at atmospheric pressure since that is the most convenient condition. However, lower or higher pressures can be used without detrimentally affecting the ultimate yield of desired product. The particular base used in the reaction is not critical, but, preferred are sodium hydroxide and potassium hydroxide.

The individual $C_{10}$-terpenyl ethers of our invention can be obtained in pure form or in substantially pure form by conventional purification techniques. Thus, the products can be purified and/or isolated by distillation, extraction, crystallization, preparative chromatographic techniques and the like. It has been found desirable to purify the $C_{10}$-terpenyl ethers by fractional distillation in vacuo.

When the $C_{10}$-terpene ethers of our invention are used as food flavor adjuvants, the nature of the co-ingredients included with said $C_{10}$-terpene ethers in formulating the product composition will also serve to alter, modify, augment or enhance the organoleptic characteristics of the ultimate foodstuff treated therewith.

As used herein in regard to flavors, the terms "alter," "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste."

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine, and a flavoring composition which incorporates one or more of the $C_{10}$-terpene ethers of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy-anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, butters and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta,-beta-dimethylacrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, damascone, α-damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpin hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alphamethylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, α-phellandrene, β-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetals (e.g., 1,1-diethoxyethane, 1,1-dimethoxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatible with the $C_{10}$-terpene ethers of our invention by not covering or spoiling the organoleptic properties (aroma and/or taste) thereof; (ii) be non-reactive with the $C_{10}$-terpene ethers of our invention and (iii) be capable of providing an environment in which the $C_{10}$-terpene ethers can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of $C_{10}$-terpene alkyl, alkenyl, haloalkenyl, and alkynyl ethers and diethers employed in a particular instance can vary over a relatively wide range, depending upon the desired organoleptic effects to be achieved. Thus, correspondingly, greater amounts would be necessary in those instances wherein the ultimate food composition to be flavored (e.g. with a spice flavor or a specific black pepper-like flavor) is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of $C_{10}$-terpene alkyl, alkenyl, haloalkenyl, and alkynyl ethers and diethers will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of $C_{10}$-terpene alkyl, alkenyl, haloalkenyl, and alkynyl ethers and diethers ranging from a small but effective amount, e.g., 0.5 parts per million up to about 100 parts per million based on total composition, are suitable. Concentrations in excess of the maximum quantity stated are not normally recommended since they fail to provide commensurate enhancement of organoleptic properties. In those instances wherein the $C_{10}$-terpene alkyl, alkenyl, haloalkenyl, and alkynyl ethers and diethers are added to the foodstuff as an integral component of a flavoring composition, it is of course essential that the total quantity of flavoring composition employed be sufficient to yield an effective $C_{10}$-terpene alkyl, alkenyl, haloalkenyl, and alkynyl ether and diether concentration in the foodstuff product.

Food flavoring compositions prepared in accordance with the present invention preferably contain the $C_{10}$-terpene alkyl, alkenyl, haloalkenyl, and alkynyl ethers and diethers in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the $C_{10}$-terpene alkyl, alkenyl, haloalkenyl, and alkynyl ethers and diethers with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and $C_{10}$-terpene alkyl, alkenyl, haloalkenyl, and alkynyl ethers and diethers in a dry blender until the requisite degree of uniformity is achieved.

It is presently preferred to combine with the $C_{10}$-terpene alkyl, alkenyl, haloalkenyl, and alkynyl ethers and diethers of our invention, the following adjuvants:
Oil of Cubeb;
Phellandrene;
β-phellandrene;
Oil of Coriander;
Oil of Pimento Leaf;
Oil of Patchouli;
Alpha Pinene;
Beta Pinene;
Beta-caryophyllene;
Dihydrocarveol;
Piperonal;
Piperine;
Chavicine;
Piperidine;
Oil of Black Pepper;
Black Pepper Oleoresin;
Capsicum;
Oil of Nutmeg.
Cardamom Oil;
Clove Oil;
Spearmint Oil; and
Oil of Peppermint.

The $C_{10}$-terpene alkyl, alkenyl, haloalkenyl, and alkynyl ethers and diethers of our invention can be used to contribute, green citrus, limey, lemony, piney, tart, herbaceous, floral, sweet anise, borneol-like, earthy carrot, petitgrain, grapefruit, deep woody animal, sandal-like woody, fruity, floral, camphoraceous, and rosemary/lavendar-like notes with basil-like, carvone-like, chamomile-like, vanillin-like nuances and sweaty undertones. As olfactory agents the $C_{10}$-terpene alkyl, alkenyl, haloalkenyl, and alkynyl ethers and diethers of our invention can be formulated into or used as components of a "perfume composition."

The term "perfume composition" is used herein to mean a mixture of organic compounds including, for example, alcohols, aldehydes, ketones, nitriles, ethers, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round-off and accompany the main note; (c) fixatives which include odorous substances which lend a particular note to the perfume throughout all stages of evaporation, and substances which retard evaporation; and (c) top-notes which are usually low-boiling, fresh-smelling materials.

In perfume compositions the individual component will contribute its particular olfactory characteristics, but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of the $C_{10}$-terpene alkyl, alkenyl, haloalkenyl, and alkynyl ether and diether of this invention which will be effective in perfume compositions depends on many factors, including the other ingredients, their amounts and the effects which are desired. It has been found that perfume compositions containing as little as 2% of the $C_{10}$-terpene alkyl, alkenyl, haloalkenyl, and alkynyl ethers and diethers of this invention, or even less, can be used to impart an interesting citrusy and/or petitgrain aroma to soaps, cosmetics, and the other products. The amount employed can range up to 50% or higher and will depend on considerations of cost, nature of the end product, and the effect desired on the finished product and particular fragrance sought.

The $C_{10}$-terpene alkyl, alkenyl, haloalkenyl, and alkynyl ethers and diethers of this invention can be used alone or in a perfume composition as a olfactory component in detergents and soaps, space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 0.01% of one or more of the $C_{10}$-terpene alkyl, alkenyl, haloalkenyl, and alkynyl ethers and diethers will suffice to impart an interesting citrusy and/or petitgrain aroma. Generally, no more than 0.5% is required.

In addition, the perfume composition can contain a vehicle or carrier for the $C_{10}$-terpene alkyl, alkenyl, haloalkenyl, and alkynyl ethers and diethers alone or with other ingredients. The vehicle can be a liquid such as an alcohol such as ethanol, a glycol such as propylene glycol, or the like. The carrier can be an absorbent solid such as a gum or components for encapsulating the composition.

The following examples are given to illustrate embodiments of the invention as it is presently preferred to practice it. It will be understood that these examples are illustrative, and the invention is not to be considered as restricted thereto except as indicated in the appended claims.

EXAMPLE I

5600 Pounds of lemons are halved, juiced and strained. The juice is diluted with a 50% volume of food-grade ethyl alcohol and centrifuged. The supernatant liquid is continuously extracted with Freon 11 for 24 hours. The extract is dried and concentrated. It is then separated into acidic, basic and neutral fractions by solvent extraction.

The methyl ester derivatives of the acidic components are then prepared by reaction with $BF_3$-methanol methylation reagent. Analysis of this fraction results in the identification of the cis and trans isomers of 1,8-dimethoxy-p-menthane. A section of the GLC profile which includes peaks for these isomers is set forth in FIG. 1A. FIG. 24 represents the NMR spectrum for 1,8-dimethoxy-p-menthane thus trapped out. FIG. 25 represents the IR spectrum for 1,8-dimethoxy-p-menthane thus trapped out.

Column chromatography of the neutral fraction on 5% water-deactivated silica gel using varying amounts of ether in isopentane results in 120 fractions which are bulked according to the GC profiles. Analysis of one such bulked fraction by GC-MS and subsequent trapping and analysis of the unknown components by NMR and IR results in the identification of carvyl ethyl ether and 8-p-cymenyl ethyl ether. Further separation of this fraction by GC area trapping, and analysis of the area traps by GC-MS results in the identification of fenchyl ethyl ether.

| GC Conditions: | Column: 500' × 0.03" Stainless steel, open tubular, SF-96 |
| --- | --- |
| | Program: 70-190° C. at 1° C./min. |
| | Nitrogen Flow Rate: 12 ml/min. |

Figure 8:
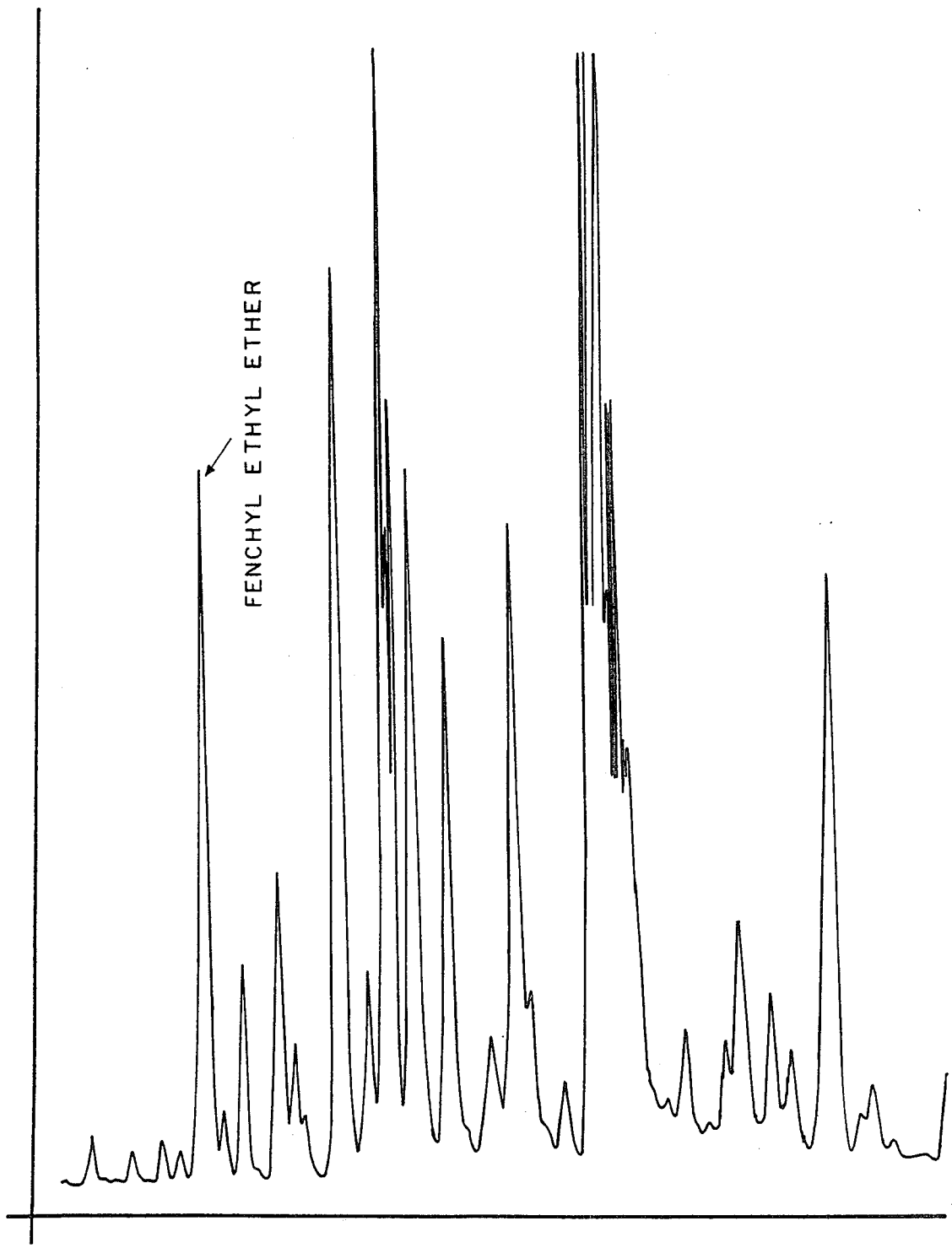
FIG. 8 is a section of the GLC profile showing the presence of fenchyl ethyl ether in lemon juice as described in Example I.

FIG. 1 represents a section of the GLC profile which includes peaks for carvyl ethyl ether and 8-p-cymenyl ethyl ether. FIG. 8 sets forth a section of the GLC profile which includes the peak for fenchyl ethyl ether.

Figure 2:
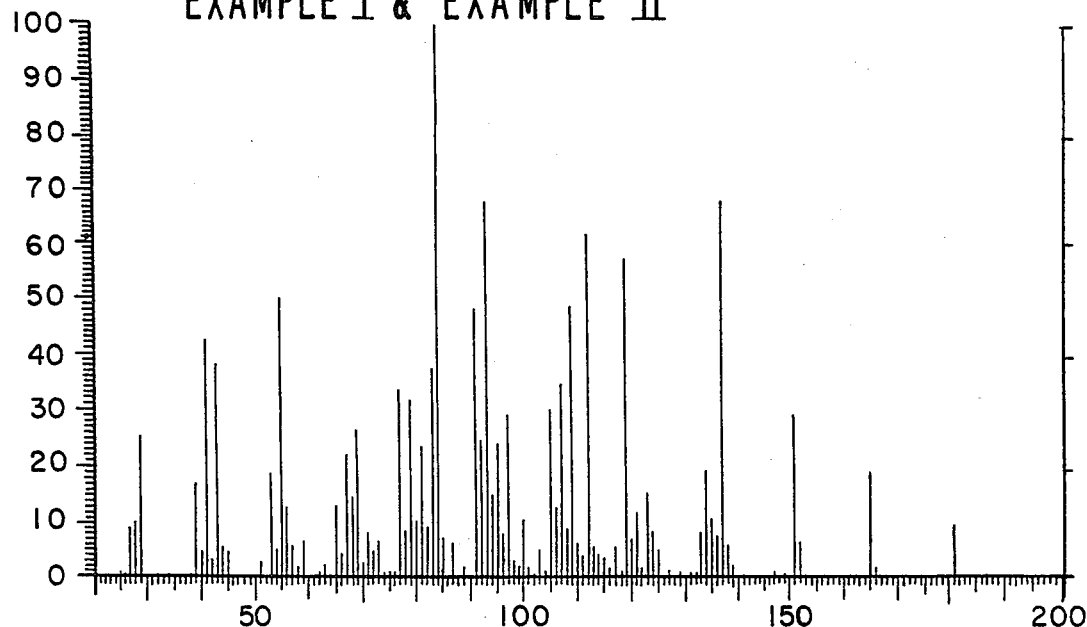
FIG. 2 represents the Mass Spectrum for carvyl ethyl ether produced according to Example I and Example II.
Figure 5:
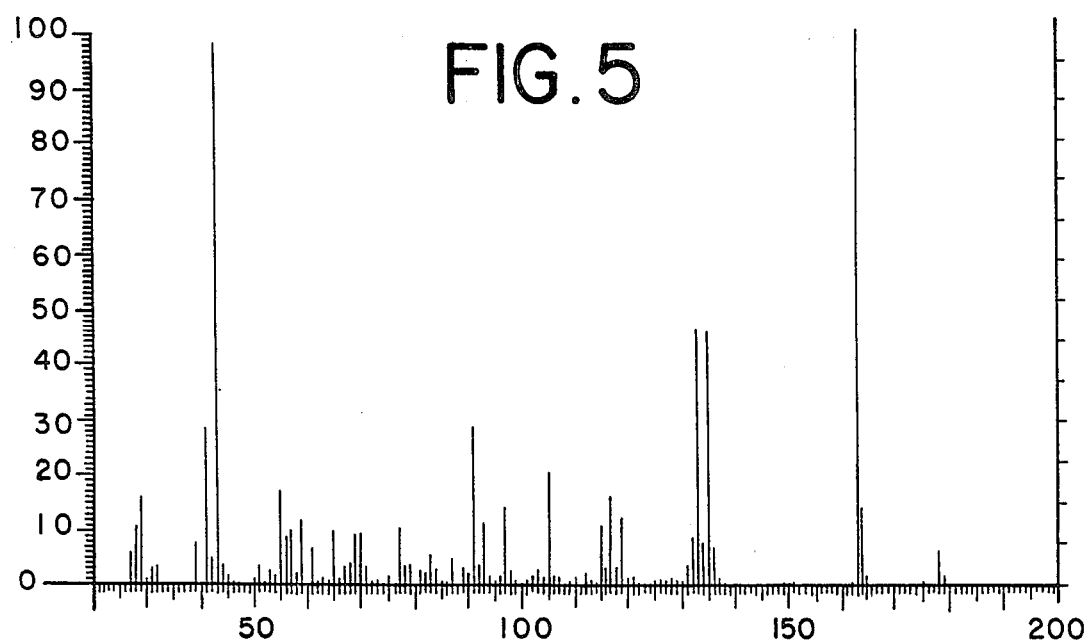
FIG. 5 represents the mass spectrum for 8-p-cymenyl ethyl ether produced according to Examples I and III.
Figure 4:
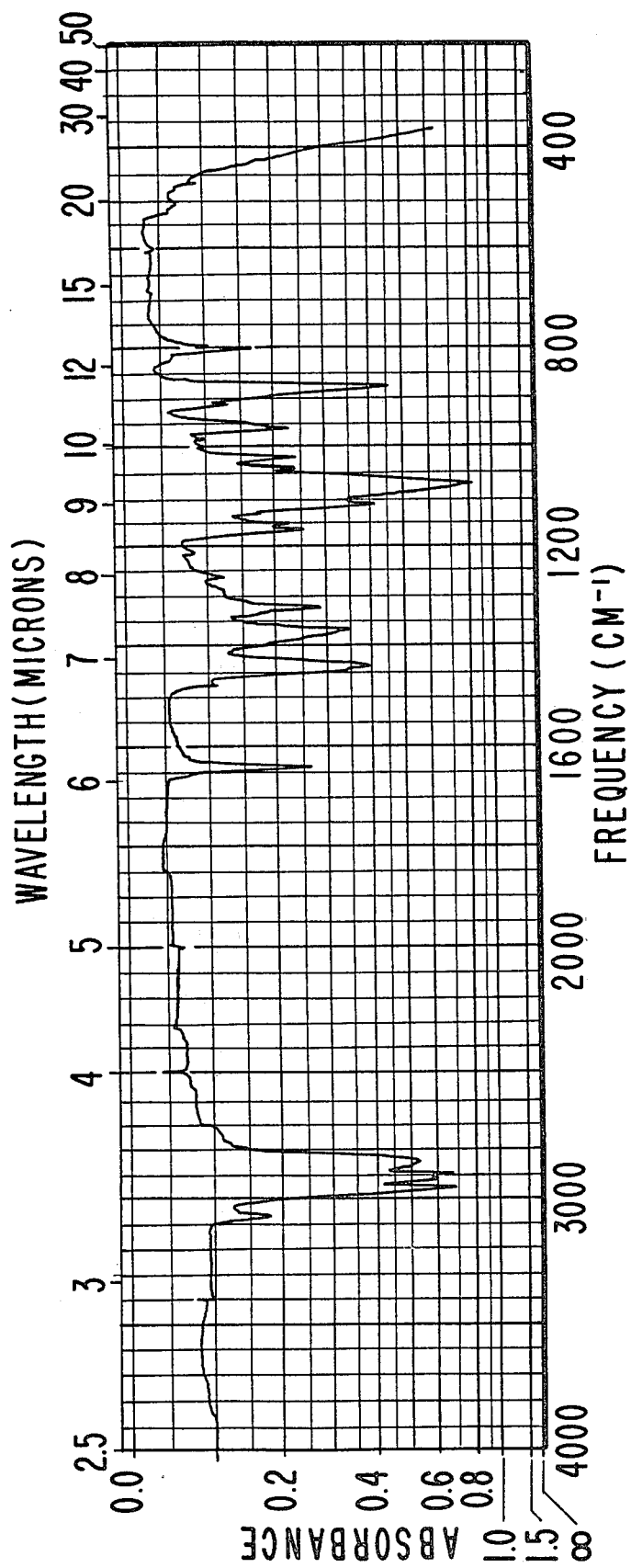
FIG. 4 represents the infrared spectrum for carvyl ethyl ether produced according to Examples I and II.
Figure 7:
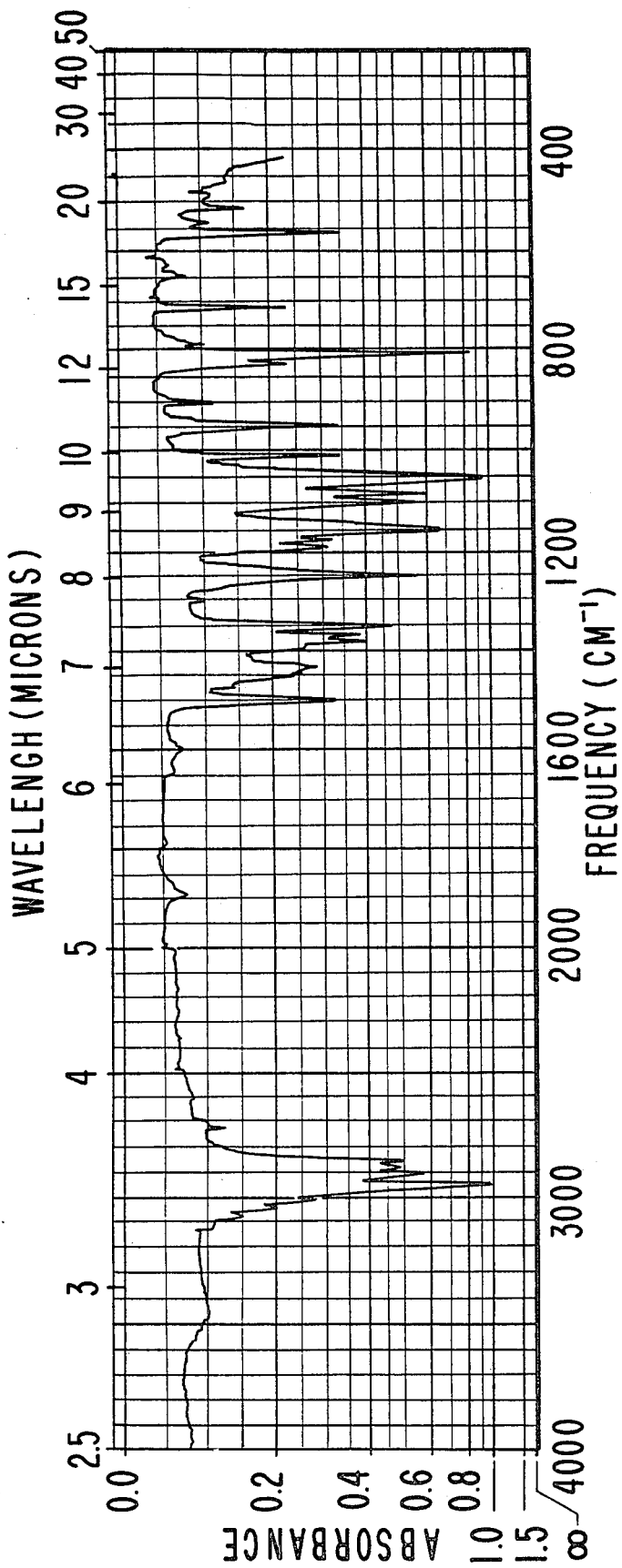
FIG. 7 represents the infrared spectrum for 8-p-cymenyl ethyl ether produced according to Examples I and III.

FIG. 2 represents the mass spectrum for carvyl ethyl ether thus trapped out. FIG. 3 represents the NMR spectrum for carvyl ethyl ether thus trapped out. FIG. 4 represents the infrared spectrum for carvyl ethyl ether thus trapped out. FIG. 5 represents the mass spectrum for 8-p-cymenyl ethyl ether thus trapped out. FIG. 6 represents the NMR spectrum for 8-p-cymenyl ethyl ether thus trapped out. FIG. 7 represents the infrared spectrum for 8-p-cymenyl ethyl ether thus trapped out. FIG. 9 represents the mass spectrum for fenchyl ethyl ether thus trapped out. FIG. 10 represents the NMR spectrum for fenchyl ethyl ether thus trapped out.

EXAMPLE II

Synthesis of Carvyl Ethyl Ether

Reaction:

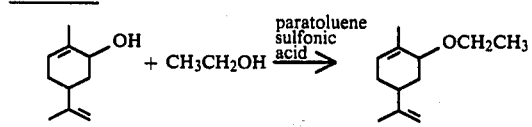

| Chemicals | |
| --- | --- |
| Carveol | 0.5 moles = 76 g |
| Ethanol | 5 moles = 230 g |
| Paratoluene sulfonic acid | 3.13 g |

Procedure

The above chemicals are placed in a 500 ml, three-necked, round bottom flask equipped with a mechanical stirrer, Friedrich's condenser and heating mantle. The mixture is heated to reflux for 24 hours, then cooled and added to 100 ml. of cold 5% NaOH solution. The aqueous layer is drawn off and the remaining layer is washed with 3×50 ml of distilled water and dried over anhydrous Na₂SO₄. 37.78 Grams of crude material is left.

The title compound is purified by distillation through a short column. Eight fractions are collected as follows:

| Fraction | Pressure (mm Hg) | Temperature | Grams |
| --- | --- | --- | --- |
| 1 | 3 | 55° C. | 1.47 |
| 2 | 3 | 75 | 0.90 |
| 3 | 3 | 78 | 7.65 |
| 4 | 3 | 85 | 4.50 |
| 5 | 3 | 87 | 1.18 |
| 6 | 3 | 92 | 3.24 |
| 7 | 3 | 96 | 2.81 |
| 8 | 3 | 98 | 1.17 |
| | | | 22.92 grams |

Fraction 8 is further purified by trapping the two major peaks from an 8'×⅛" 20% Carbowax 20 M column. (Conditions: programmed at 80°-190° C. at 4° C./min.) The peaks are identified as isomers of 2,8-diethoxy-p-menthane.

Fraction 3 is analyzed via MS-GC. The major peak is the title compound. The compound is trapped from an 8'×⅛" 10% Carbowax 20 M packed column (programmed at 80°-190° C. at 4° C./min).

The mass spectrum for the carvyl ethyl ether is set forth in FIG. 2. The NMR spectrum for carvyl ethyl ether is set forth in FIG. 3. The IR spectrum for carvyl ethyl ether is set forth in FIG. 4.

EXAMPLE III

Synthesis of 8-p-Cymenyl Ethyl Ether

Reaction:

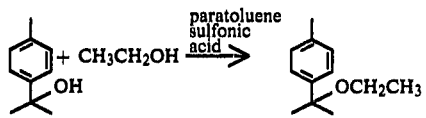

| Chemicals | |
| --- | --- |
| 8-p-cymenol | 44.5 g (0.297 moles) |
| ethanol | 136.6 g (2.97 moles) |
| paratoluene sulfonic acid | 1.86 g |

Procedure

The above chemicals are placed in a 250 ml, three-necked, round-bottom flask equipped with a Friedrich's condenser, mechanical stirrer and heating mantle. The resulting mixture is heated to reflux until the GC indicates that the reaction has gone to completion. The reaction mass is cooled to room temperature and neutralized with a saturated Na₂CO₃ solution. Then the aqueous phase is extracted with three 100 ml portions of methylene chloride. The methylene chloride extract is dried over anhydrous Na₂SO₄ and stripped on a rotary evaporator. The mixture is fractionated on a gas chromatograph, and three major peaks are eluted, two of them match 8-p-cymenol and the third is unknown. The title compound is purified by preparative gas chromatography.

Conditions

12'×0.375" 10% SE-30 column;
140° C. Isothermal;
Feed Rate: 250 μl/min

A total of 0.35 g is collected for evaluation (purity=98.82%).

The mass spectrum for 8-p-cymenol ethyl ether is set forth in FIG. 5. The NMR spectrum for 8-p-cymenol ethyl ether is set forth in FIG. 6. The IR spectrum for 8-p-cymenol ethyl ether is set forth in FIG. 7.

EXAMPLE IV(A)

Synthesis of Isobornyl Ethyl Ether

Reaction:

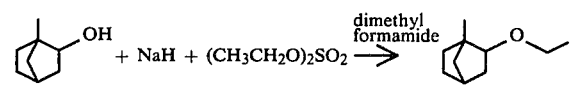

| Chemicals | |
| --- | --- |
| Isoborneol | 1 mole = 154 g |
| NaH | 1 mole = 48 g (50% in mineral oil) |
| Diethyl sulfate | 1.1 mole = 169.4 g |
| DMF (dimethyl formamide) | 500 ml. |
| Triethyl borate | 80.3 g |

Procedure

The NaH and DMF (400 ml) are added to a two liter, round-bottom flask equipped with an $N_2$ bubbler, vented Friedrich's condenser, mechanical stirrer and additional funnel. $CaCl_2$ Drying tubes are placed on all open ends. $N_2$ Is bubbled into the flask to evacuate the air. Isoborneol is then dissolved in 100 ml of DMF and placed in the addition funnel. The isoborneol is then added dropwise to the reaction mass. When the isoborneol addition is complete, the mixture is heated until no more $H_2$ is given off. The reaction mass is then cooled to room temperature, and the diethyl sulfate is added dropwise. The reaction is slightly exothermic. After all of the diethyl sulfate is added, GC analysis indicates that less than 0.3% of the diethyl sulfate is present.

The mixture is cooled to room temperature, and one liter of water is slowly added thereto over a period of one hour. Two layers are present, the top layer being drawn off and saved. The aqueous layer is extracted with two 250 ml portions of diethyl ether. The ether layer is combined with the top layer and dried over anhydrous $Na_2SO_4$; then stripped by rotary evaporator. 152.97 Grams of crude material remains, GC yield=54.89%.

The 152.97 grams of crude material plus 80.3 grams (0.55 moles) of triethyl borate are placed in a 500 ml flask equipped with a 12" Vigreaux column and distillation head. The contents are heated at atmospheric pressure until the pot temperature reaches 160° C. (within 1 hour).

The resulting material is then transferred to a fractional distillation apparatus and fractionally distilled (distillation conditions: 62°-68° C. at 2.0-2.4 mm Hg pressure).

The total weight of combined fractions 3-8 amounts to 50.65 g (actual yield—28%) of material over 94% pure. Fraction #8 is subjected to MS, NMR and IR analyses. The NMR analysis indicated that the composition is isobornyl ethyl ether.

EXAMPLE IV(B)

Synthesis of Fenchyl Ethyl Ether

Reaction:

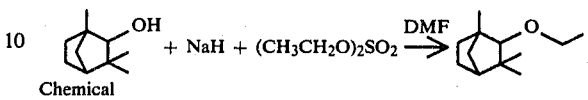

| Chemical | |
| --- | --- |
| Fenchyl alcohol | 154 g (1M) |
| Sodium hydride | 48 g of 50% in mineral oil (1M) |
| Diethyl sulfate | 169.4 g (1M) |
| DMF (dimethyl formamide) | 500 ml |

Procedure

The reaction is carried out and extracted in the same manner as described in Example IV(A), supra (SYNTHESIS OF ISOBORNYL ETHYL ETHER). The yield of crude material after the ether is stripped is 170.80 g. G.C. yield=43.4%.

The 170.8 g of crude material is added to 74.2 g of triethyl borate and distilled at atmospheric pressure as in Example IV(A).

The material left in the pot is then transferred to a fractional distillation apparatus and distilled at 66°-67° C. at 5 mm Hg pressure. Fraction #5 is subjected to MS, NMR and IR analyses. The percent yield based on Fractions 4-6 combined is 23.3%.

FIG. 9 represents the mass spectrum for fenchyl ethyl ether produced according to Example IV(B). FIG. 10 represents the NMR spectrum for fenchyl ethyl ether. FIG. 11 represents the infrared spectrum for fenchyl ethyl ether.

What is claimed is:

1. A process for flavoring a foodstuff or chewing gum to impart a herbal, coumarin-like and green aroma characteristic with herbal, cumin-like, lemon juice-like, green, and oily flavor characteristics comprising the step of adding to a foodstuff or chewing gum from 0.5 ppm up to about 100 ppm of synthetically produced substantially pure 8-p-cymenyl ethyl ether having the structure:

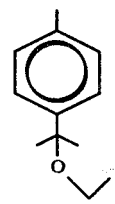

* * * * *